(12) United States Patent
McLean et al.

(10) Patent No.: US 12,251,308 B2
(45) Date of Patent: Mar. 18, 2025

(54) DELIVERY SYSTEMS FOR CARDIAC VALVE DEVICES

(71) Applicant: Half Moon Medical, Inc., Menlo Park, CA (US)

(72) Inventors: Matthew McLean, San Francisco, CA (US); Gaurav Krishnamurthy, Mountain View, CA (US); Hanson S. Gifford, III, Woodside, CA (US); Neil Zimmerman, Menlo Park, CA (US)

(73) Assignee: Half Moon Medical, Inc., Menlo Park, CA (US)

( * ) Notice: Subject to any disclaimer, the term of this patent is extended or adjusted under 35 U.S.C. 154(b) by 658 days.

(21) Appl. No.: 17/595,427

(22) PCT Filed: May 18, 2020

(86) PCT No.: PCT/US2020/033478
§ 371 (c)(1),
(2) Date: Nov. 16, 2021

(87) PCT Pub. No.: WO2020/236757
PCT Pub. Date: Nov. 26, 2020

(65) Prior Publication Data
US 2022/0192822 A1 Jun. 23, 2022

Related U.S. Application Data

(60) Provisional application No. 62/850,406, filed on May 20, 2019.

(51) Int. Cl.
*A61F 2/24* (2006.01)
(52) U.S. Cl.
CPC ............ *A61F 2/243* (2013.01); *A61F 2/2439* (2013.01); *A61F 2220/0033* (2013.01); *A61F 2230/0013* (2013.01)

(58) Field of Classification Search
CPC ...... A61F 2/243; A61F 2/2439; A61F 2/2436; A61F 2002/9505; A61F 2002/9511;
(Continued)

(56) References Cited

U.S. PATENT DOCUMENTS 8,870,855 B2 * 10/2014 Fargahi ................... A61F 2/966
606/1
9,649,212 B2 5/2017 Fargahi
(Continued)

FOREIGN PATENT DOCUMENTS

JP 2012005846 4/2013
JP 2015-517376 6/2015
(Continued)

OTHER PUBLICATIONS

International Search Report and Written Opinion mailed Jul. 24, 2020 in International Patent Application No. PCT/US2020/033478, 11 pages.
(Continued)

*Primary Examiner* — Paul B Prebilic
(74) *Attorney, Agent, or Firm* — Perkins Coie LLP

(57) ABSTRACT

Delivery systems for placing an implantable cardiac device at a native comprising a delivery catheter and an attachment assembly. The delivery catheter can include a proximal portion and a distal portion, and the attachment assembly can be at the distal portion of the delivery catheter. The attachment assembly can include arm pairs in which individual arm pairs include a first arm with connector and a second arm with a retainer. Each first arm extends along a corresponding second arm, and the first arm and/or the second arm in each arm pair moves relative to the other from a locked position to a released position. In the locked position, the retainer interfaces with the connector to maintain engagement between the implantable device and the
(Continued)

connector. In the released position, the retainer is positioned relative to the connector such that the implantable device can disengage the connector.

32 Claims, 15 Drawing Sheets

(58) Field of Classification Search
CPC .............. A61F 2/966; A61F 2220/0033; A61F 2220/0075; A61F 2230/0013; A61F 2250/0008
See application file for complete search history.

(56) References Cited

U.S. PATENT DOCUMENTS

| | | | |
|---|---|---|---|
| 9,750,606 B2 | 9/2017 | Ganesan et al. | |
| 10,653,521 B2 | 5/2020 | Dienno et al. | |
| 10,799,361 B2 | 10/2020 | Hauser et al. | |
| 2010/0049313 A1 | 2/2010 | Alon et al. | |
| 2013/0123898 A1* | 5/2013 | Tung | A61F 2/2436 623/1.11 |
| 2014/0249621 A1* | 9/2014 | Eidenschink | A61F 2/2439 623/2.11 |
| 2015/0127093 A1* | 5/2015 | Hosmer | A61F 2/2427 623/2.11 |
| 2015/0173897 A1* | 6/2015 | Raanani | A61F 2/2436 623/2.11 |
| 2016/0354106 A1* | 12/2016 | Losordo | A61F 2/95 |
| 2017/0231765 A1* | 8/2017 | Desrosiers | A61F 2/2436 623/2.11 |
| 2017/0325950 A1* | 11/2017 | Calomeni | A61F 2/2436 |
| 2018/0311036 A1 | 11/2018 | Backus et al. | |
| 2021/0015608 A1 | 1/2021 | Hauser et al. | |
| 2022/0192822 A1* | 6/2022 | McLean | A61F 2/95 |

FOREIGN PATENT DOCUMENTS

| | | |
|---|---|---|
| WO | 2012009006 | 1/2012 |
| WO | WO2012009006 A1 | 1/2012 |
| WO | 2013175468 | 11/2013 |
| WO | WO2013175468 A2 | 11/2013 |
| WO | 2017035381 | 3/2017 |
| WO | WO2017035381 A1 | 3/2017 |
| WO | 2017196914 | 11/2017 |
| WO | WO2017196914 A1 | 11/2017 |

OTHER PUBLICATIONS

International Search Report and Written Opinion mailed Feb. 18, 2022 in International Patent Application No. PCT/US2021/050538, 13 pages.
Office Action for Japanese Application No. 2021-569282 mailed Feb. 29, 2024, 4 pages with English translation.

* cited by examiner

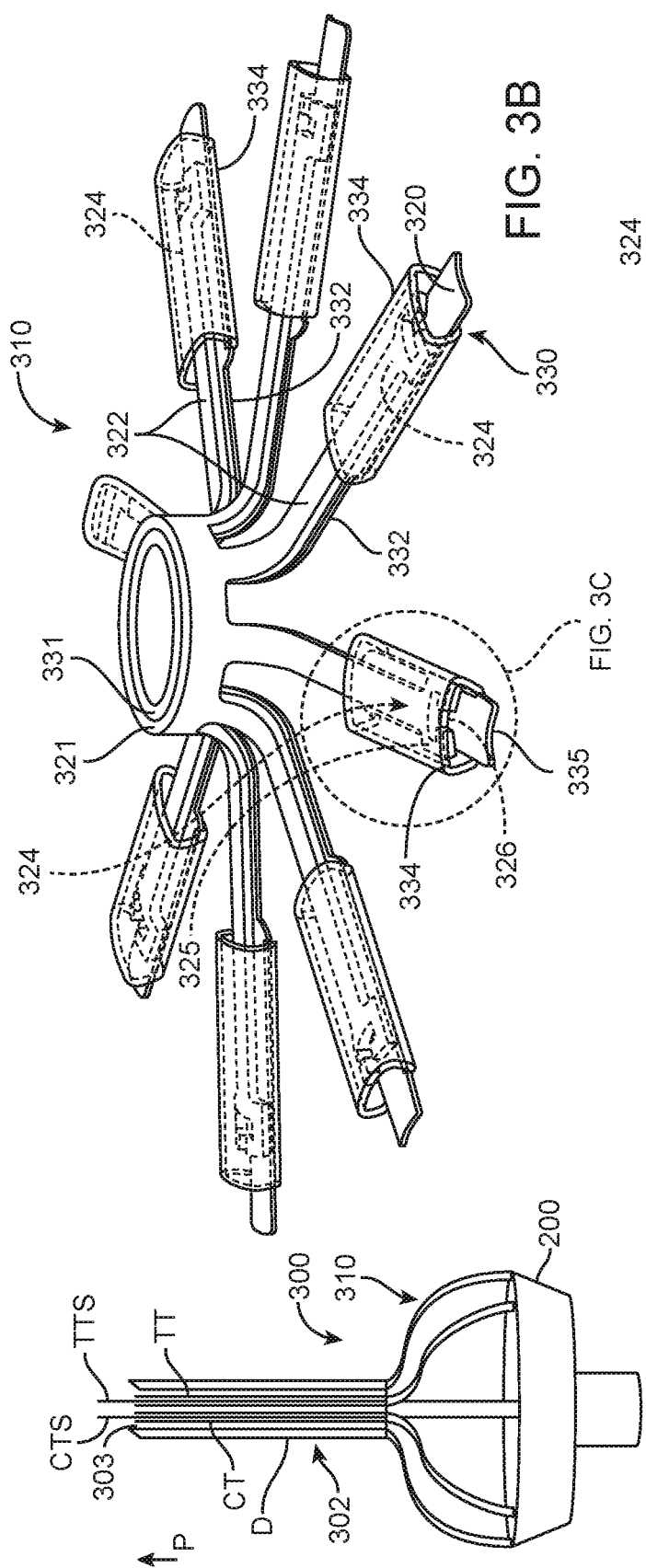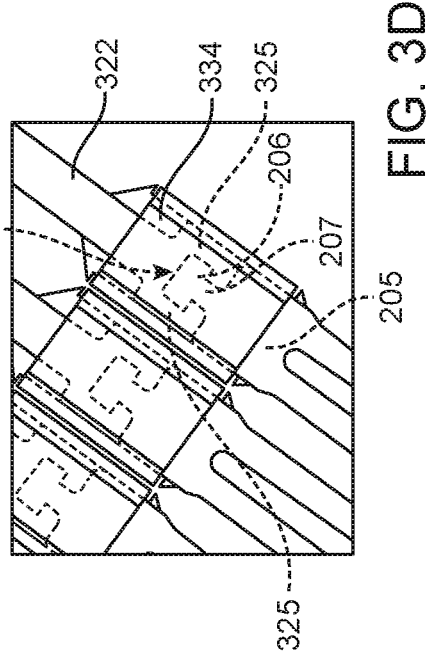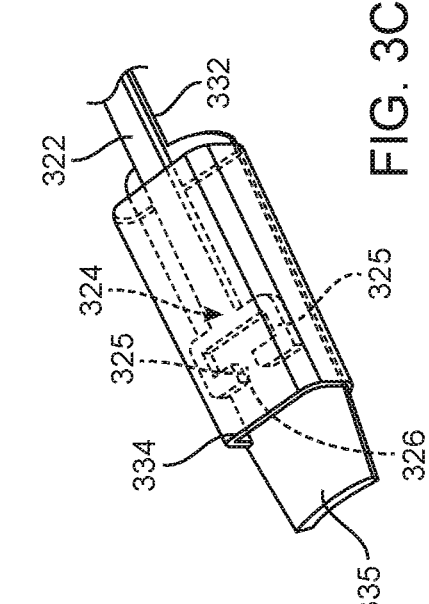

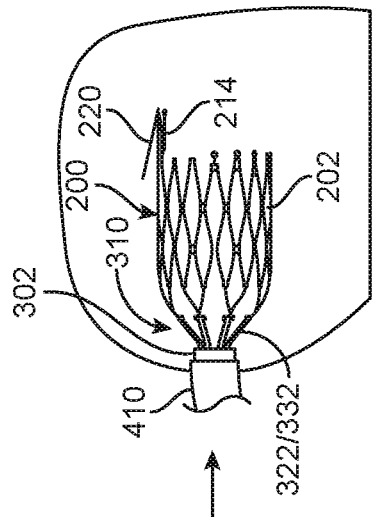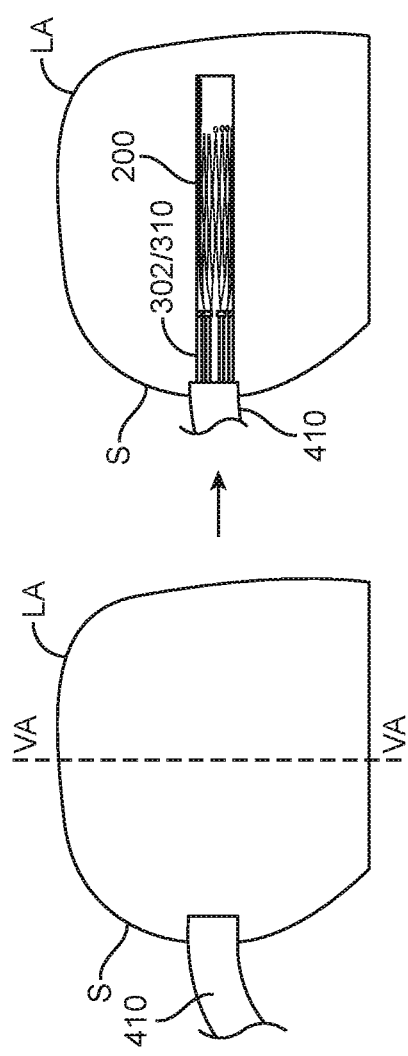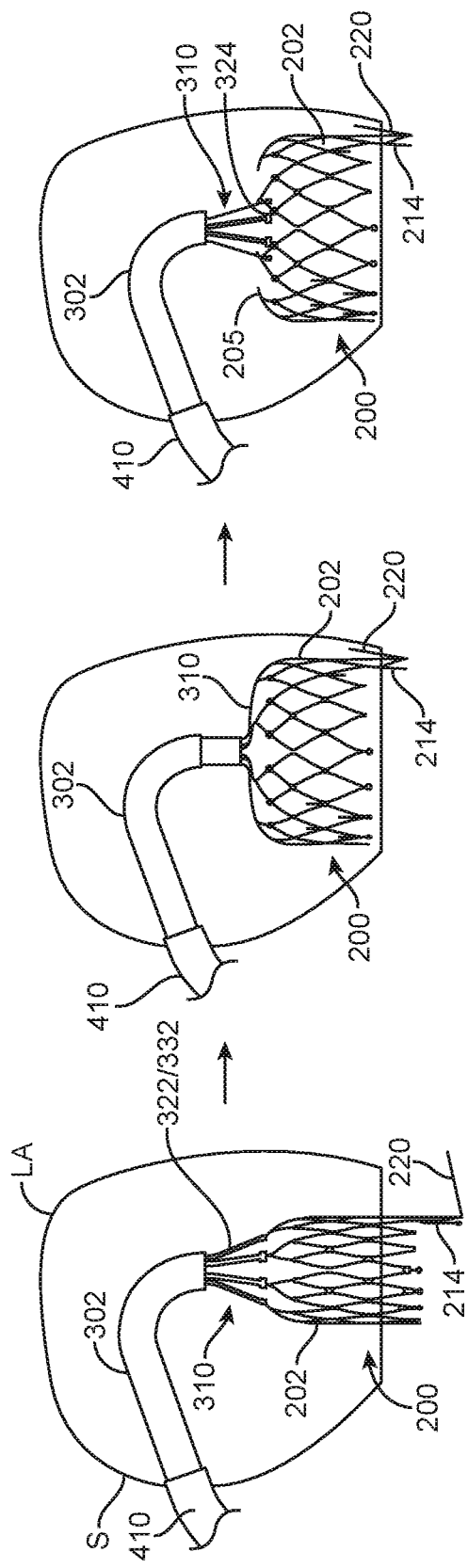

DELIVERY SYSTEMS FOR CARDIAC VALVE DEVICES

CROSS-REFERENCE TO RELATED APPLICATION(S)

This application is a 35 U.S.C. § 371 U.S. National Phase application of International Patent Application No. PCT/US2020/033478, filed May 18, 2020, which claims priority to and the benefit of U.S. Provisional Application No. 62/850,406, filed May 20, 2019, each of which is incorporated herein by reference in its entirety.

TECHNICAL FIELD

Delivery systems for implanting cardiac valve devices via a minimally invasive endovascular approach or via a mini-thoracotomy.

BACKGROUND

Proper functioning of the mitral valve can be affected by mitral valve regurgitation, mitral valve prolapse, or mitral valve stenosis. Mitral valve regurgitation can occur when the leaflets of the mitral valve fail to coapt into apposition at peak contraction pressures such that blood leaks from the left ventricle into the left atrium. Several structural factors may affect the proper closure of the mitral valve leaflets. For example, an enlarged mitral annulus caused by dilation of heart muscle may prevent proper coaptation of the leaflets during systole. Other conditions involve a stretch or tear in the chordae tendineae, the tendons connecting the papillary muscles to the inferior side of the mitral valve leaflets, which may also affect proper closure of the mitral annulus. A ruptured chordae tendineae, for example, may cause a valve leaflet to prolapse into the left atrium due to inadequate tension on the leaflet. Abnormal backflow can also occur when the papillary muscles are compromised (e.g., due to ischemia) such that the affected papillary muscles do not contract sufficiently to effect proper closure during systole.

Mitral valve prolapse can occur when the mitral leaflets abnormally bulge up in to the left atrium, which can also lead to mitral valve regurgitation. Normal functioning of the mitral valve may also be affected by mitral valve stenosis, or a narrowing of the mitral valve orifice, which impedes of filling of the left ventricle during diastole.

Mitral valve regurgitation is often treated using diuretics and/or vasodilators to reduce the amount of blood flowing back into the left atrium. Other treatment methods, such as surgical approaches (open and intravascular), have also been used to either repair or replace the native mitral valve. For example, cinching or resecting portions of the dilated annulus are typical repair approaches.

Cinching of the annulus has been accomplished by implanting annular or peri-annular rings which are generally secured to the annulus or surrounding tissue. Other repair procedures have also involved suturing or clipping of the valve leaflets into partial apposition with one another.

Alternatively, more invasive procedures replace the entire valve with mechanical valves or biological tissue. These invasive procedures are conventionally done through large open thoracotomies and are thus very painful, have significant morbidity, and require long recovery periods.

However, with many repair and replacement procedures, the durability of the devices or improper sizing of annuloplasty rings or replacement valves may cause complications. Moreover, many of the repair procedures depend upon the skill of the cardiac surgeon since poorly or inaccurately placed sutures may affect the success of procedures.

Compared to other cardiac valves, the mitral valve presents unique challenges because portions of the mitral valve annulus have limited radial support from surrounding tissue and the mitral valve has an irregular, unpredictable shape. For example, the anterior wall of the mitral valve is bound by only a thin wall separating the mitral valve annulus from the inferior portion of the aortic outflow tract. As a result, significant radial forces on the mitral valve annulus are not acceptable as they could lead to collapse of the inferior portion of the aortic tract with potentially fatal consequences. Another challenge of the mitral valve anatomy is that the maze of chordae tendineae in the left ventricle makes navigating and positioning a deployment catheter much more difficult compared to other heart valves. Given the difficulties associated with current procedures, there remains the need for simple, effective, and less invasive devices and methods for treating dysfunctional heart valves. Additionally, since it is also difficult to deliver devices to the mitral valve, there also remains the need for effective and less invasive delivery systems to deliver the implantable cardiac devices to the mitral valve.

BRIEF DESCRIPTION OF THE DRAWINGS

FIG. 3A shows a portion of a delivery catheter and an attachment assembly of a delivery system in accordance with the present technology attached to an implantable device;

FIG. 3B is a view of the attachment assembly of a delivery system in accordance with the present technology;

FIGS. 3C-3E are views of connectors of attachment assemblies for attaching the delivery system to an implantable device in accordance with the present technology;

FIGS. 4A-4F show aspects of operating delivery systems in accordance with the present technology to position an implantable device relative to the anatomy of a native cardiac valve;

DETAILED DESCRIPTION

Disclosed herein are examples of delivery systems for implanting a medical device, such as a valve repair device or a prosthetic heart valve, in a native heart. In some embodiments, delivery systems for placing an implantable cardiac device at a native heart valve comprise a delivery catheter and an attachment assembly. The delivery catheter can include a proximal portion and a distal portion, and the attachment assembly can be at the distal portion of the delivery catheter. The attachment assembly can include arm pairs in which individual arm pairs include a first arm with a connector and a second arm with a retainer. Each first arm extends along a corresponding second arm, and the first arm and/or the second arm in each arm pair moves relative to the other from a locked position to a released position. In the locked position, the retainer interfaces with the connector to maintain engagement between the implantable device and the connector. In the released position, the retainer is positioned relative to the connector such that the implantable device can disengage the connector.

Figure 1:
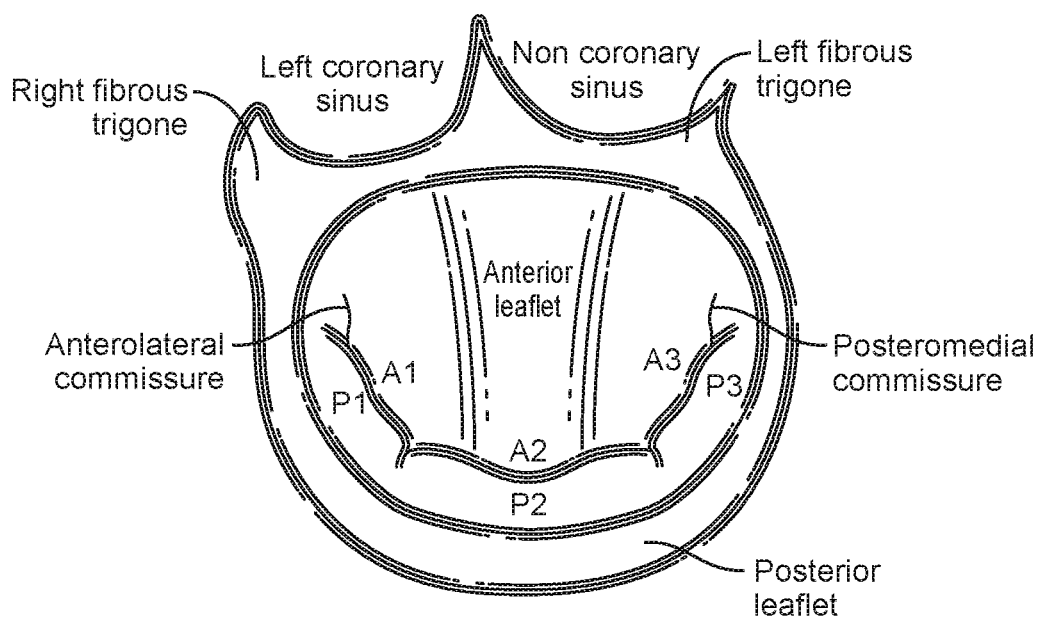
FIG. 1 is a diagram of a mitral valve.

FIG. 1 shows a mitral valve which may be accessed by a delivery system according to the present technology. The anterior leaflet has a semi-circular shape and attaches to two-fifths of the annular circumference. The motion of the anterior leaflet defines an important boundary between the inflow (diastole) and outflow (systole) tracts of the left ventricle. The posterior leaflet of the mitral valve has a crescent shape and is attached to approximately three-fifths of the annular circumference. The posterior leaflet typically has two well-defined indentations which divide the leaflet into three individual scallops identified as P1 (lateral scallop), P2 (middle scallop), and P3 (medial scallop). The three corresponding segments of the anterior leaflet are identified as A1 (anterior segment), A2 (middle segment), and A3 (posterior segment). The leaflet indentations aid in opening the posterior leaflet during diastole.

As shown in FIG. 1, the mitral valve has anterolateral and posteromedial commissures which define a distinct area where the anterior and posterior leaflets come together at their insertion into the annulus. Sometimes the commissures exist as well-defined leaflet segments, but often this area is a subtle structure that can be identified using the following two anatomic landmarks: (a) the axis of corresponding papillary muscles, and (b) the commissural chordae, which have a specific fan-like configuration. Several millimeters of valvular tissue separate the free edge of the commissures from the annulus.

The mitral valve is an atrio-ventricular valve separating the left atrium from the left ventricle. The mitral annulus constitutes the anatomical junction between the left ventricle and the left atrium. The fixed ends of the leaflets are attached to the annulus. The anterior portion of the mitral annulus is attached to the fibrous trigones and is generally more developed than the posterior annulus. The right fibrous trigone is a dense junctional area between the mitral valve, tricuspid valve, non-coronary cusp of the aortic valve, and the membranous septum. The left fibrous trigone is situated at the junction of both left fibrous borders of the aortic valve and the mitral valve.

The mitral annulus is less well developed at the insertion site of the posterior leaflet. This segment is not attached to any fibrous structures, and the fibrous skeleton in this region is discontinuous. This posterior portion of the annulus is prone to increase its circumference when mitral regurgitation occurs in association with left atrial or left ventricular dilation. The mitral annulus is saddle-shaped, and during systole the commissural areas move proximally, i.e. towards the roof of the atrium, while annular contraction also narrows the circumference. Both processes aid in achieving leaflet coaptation, which may be adversely affected by annular dilatation and calcification. The mitral annulus is surrounded by several important anatomic structures, including the aortic valve, the coronary sinus, and the circumflex artery. As a result, implanted cardiac devices at the mitral valve need to be positioned to accommodate the asymmetrical anatomy of the mitral valve without impacting the surrounding cardiac structures.

Figure 2:
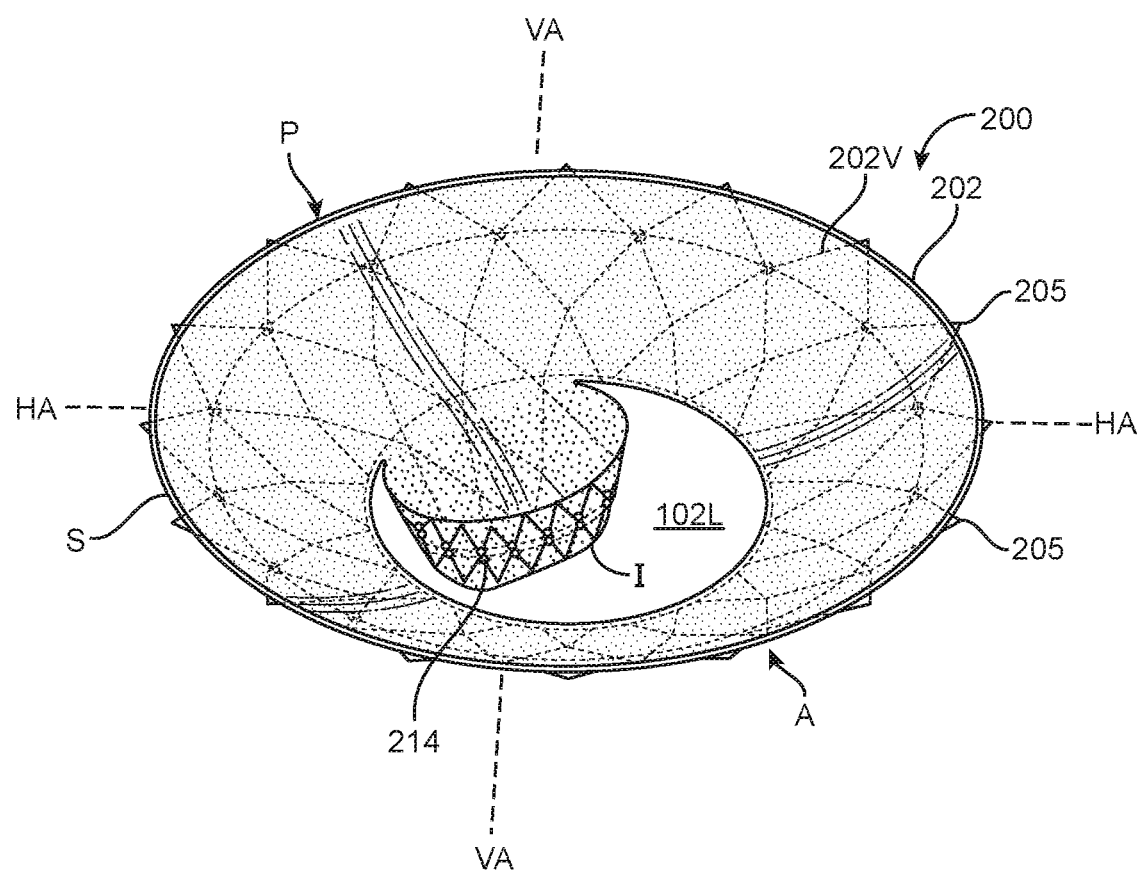
FIG. 2 depicts an implantable device, such as a cardiac valve device, that can be delivered to a native human heart using delivery devices in accordance with the present technology.

FIG. 2 is an isometric view showing an example of an implantable device 200, such as a prosthetic leaflet device, which may be delivered to the heart using delivery systems according to the present technology. The implantable device 200 can be a prosthetic leaflet device having an atrial-fixation member 202 and a baffle 214 depending from the atrial-fixation member 202 in a downstream direction. The atrial-fixation member 202 can be configured to position and hold the baffle 214 at a desired location with respect to the native valve anatomy, and the baffle 214 is configured to displace at least a portion of a native leaflet of the cardiac valve and create a prosthetic coaptation surface for at least a portion of one or more of the other native leaflets of the cardiac valve. The baffle 214 can have a normally-closed clip 220 (see, FIG. 4C) depending from its posterior surface which can be opened to engage the ventricular side of one of the native leaflets. A tendon (made of suture or nitinol wire) can actuate the clip by way of a lever attached to the clip. The lever may be a nitinol wire or laser cut nitinol or Co—Cr sheet. Additional implantable devices that can be used with delivery systems in accordance with the present technology are described in PCT/US2018/043566, which is incorporated herein in its entirety by reference. Any of several prosthetic valve replacement devices could similarly be used with delivery systems in accordance with the present technology, including complete mitral valve replacement devices. And, in addition to mitral valves, other valves such as tricuspid, aortic, and pulmonic valves could also be delivered using delivery systems in accordance with the present invention.

The implantable device 200 is configured relative to a flow axis VA in the direction of blood flow from the atrium to the ventricle and a transverse axis HA at an angle (e.g., orthogonal) to the flow axis VA. The implantable device 200 has a posterior side P, an anterior side A, a superior end S and an inferior end I. The implantable device 200 has a proximal or leading end which faces the atrium and a distal or trailing end which faces the ventricle. The uppermost row of struts of the atrial-fixation member 202 of the implantable device 200 includes a plurality of inverted V-shaped structures or crown points (e.g., chevrons) 202V. One or more of the chevrons 202V may each include a connector 205 at the apex of the inverted V-shaped crown points. The connectors 205 are sized to engage with a mating feature on the delivery system (described below).

The implantable device 200 may be inserted via a femoral vein sheath to traverse the inferior vena cava to the right atrium. The implantable device is then inserted into the left atrium via a puncture of the interatrial septum. In several applications, the implantable device 200 is desirably delivered to a target location within the mitral valve to function properly. This means appropriate positioning along the flow axis, correct radial positioning relative to the central axis of the valve, correct rotational orientation to specific landmarks such as the middle (P2) portion of the native posterior leaflet, and correct angular positioning relative to the flow axis and the transverse axis. The implantable device 200 may also need to be repositioned during the delivery process. For example, the implantable device 200 may initially be positioned distally into the left ventricle of the heart to engage one or more native valve leaflets, and then moved proximally towards the left atrium of the heart for final positioning before being released from the delivery system. Releasing the implantable device 200 from the delivery system should not exert excessive forces against the implantable device 200 or cause the implantable device 200 to move after being placed at the desired location and in the desired orientation relative to the native valve. Furthermore, the delivery system should allow the implantable device to be re-sheathed, repositioned, and/or removed before being released from the delivery system. Delivery systems of the present technology can achieve all the above-mentioned advantages in a user-friendly system. Additionally, several embodiments of delivery systems in accordance with the present technology have a small overall diameter, such as approximately 15 to 30 French.

FIGS. 3A-3C depict an example of a distal portion of a delivery system 300 of the present technology. Referring to FIG. 3A, the system 300 includes a delivery catheter 302 and an attachment assembly 310 configured to (a) securely retain the implantable device 200 as it passes through the vasculature (or through a guide that was previously placed through the vasculature and the atrial septum) and (b) selectively release the implantable device 200 at a desired target site. The delivery catheter 302 can have a proximal portion P and a distal portion D, and the attachment assembly 310 can be at the distal portion D of the delivery catheter 302. The system 300 may optionally include at least one cinching tube CT containing a double-length suture loop CTS used to radially compress the atrial-fixation member 202. The system 300 may further optionally include a tendon tube TT containing a double-length suture loop TTS used to open the clip on the posterior side of the baffle 214. The tendon path may be configured so that actuating the tendon opens the clip. The optional cinching tube CT and tendon tube TT may extend through a lumen 303 in the delivery catheter 302. It may also be possible to simply provide the suture CTS and TTS within lumens defined in the wall of the delivery catheter 302 or the central lumen of the delivery catheter 302, with short, flexible tubes extending distally from the tip of the catheter to the implant.

Referring to FIG. 3B, the attachment assembly 310 has a connector mechanism 320 and a locking mechanism 330. The connector mechanism 320 can have a first actuator 321 (only a distal portion is shown), first arms 322 extending from a distal end of the first actuator 321, and a connector 324 at the end of each first arm 322. The first actuator 321 can be a first tube or first hub. The locking mechanism 330 can have a second actuator 331 (only a distal portion is shown), second arms 332 extending from the distal end of the second actuator 331, and a retainer 334 at the end of each second arm 332. The second actuator 331 can be a second tube or second hub. Each first arm 322 can be aligned with a corresponding second arm 332 such that the attachment assembly 310 has several pairs of first and second arms 322 and 332, respectively. The first and second arms 322 and 332 can be directly superimposed over/under each other as shown, or they can be side-by-side, or they can have other suitable configurations. In the embodiment shown in FIG. 3B, the attachment assembly 310 has eight arm pairs of first and second arms 322/332, but it can have any number of arm pairs, such as 2, 3, 4, 5, 6, 7, 8, 9, 10, 11, 12, or more.

FIG. 3C is a detailed view showing the interface between a connector 324 and a retainer 334 of a single arm pair 322/332. In some embodiments, the connector 324 is a C-shaped member having fingers 325 that extend from the corresponding first arm 322 and a central opening 326 between the distal ends of the fingers 325. In some embodiments, the retainer 334 is a sleeve configured to slide over the connector 324 for moving from a locked position (shown in FIG. 3C) to a release position (not shown) proximal of the locked position. The second arms 332 can have extensions 335 at their ends.

FIG. 3D is a detailed view of the interface between a connector 205 of an implantable device 200 (FIG. 2), a connector 324 and a retainer 334. The C-shaped configuration of the fingers 325 can be configured to receive the connector 205 of the implantable device 200. For example, the connector 205 can have a head 206 configured to be retained between the fingers 325 and a neck 207 configured to extend through the opening 326 between the fingers 325. FIG. 3D shows the retainer 334 in the locked position in which the retainer 334 securely retains the head 206 of the connector 205 between the fingers 325. In the locked position, the retainer 334 prevents the connector 205 from disengaging the connector 324. To move to the released position, the retainer 334 is positioned proximally relative to the connector 324 along the lengthwise dimension of the first arm 322 such that the head 206 and the neck 207 can disengage the connector 324. For example, the first and second actuators 321 and 331 (FIG. 3B) can move relative to each other such that the first and second arms 322 and 332 (FIG. 3B) slide relative to each other along their lengthwise dimension. In one embodiment, the second actuator 331 is pulled proximally relative to the first actuator 321 such that the retainer 334 moves proximally relative to the connector 324. In another embodiment, the first actuator 321 is pushed distally relative to the second actuator 331 such that the connector 324 moves distally relative to the retainer 334. In either case, the connector 324 is positioned distal of the retainer 334 such that the connector 205 can disengage the connector 324.

Figure 3E:
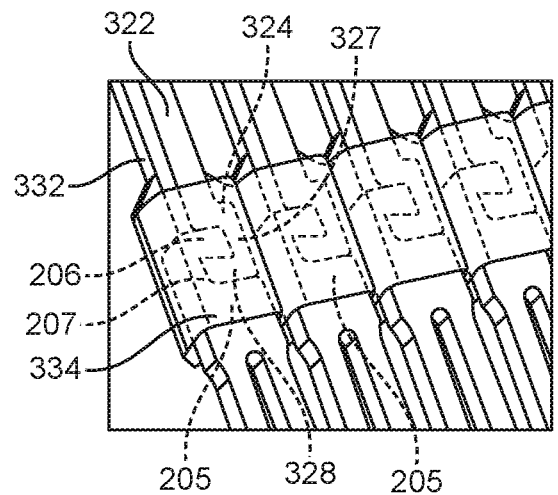

FIG. 3E is a detailed view of another configuration of the connecter 324 at the end of one of the first arms 322 and another configuration of the connector 205 of the implantable device 200. In this embodiment, the connector 324 is a hooked-shaped member having a neck 327 and a head 328, and the connector 205 is a mating hooked-shaped member having a neck 207 and a head 206. The connector 205 mates with the connector 324 such that the heads 328 and 206 engage each other in a manner that prevents the implantable device 200 from disengaging the connector 324 when the retainer 334 is in the locked position shown in FIG. 3E.

Figure 3F:
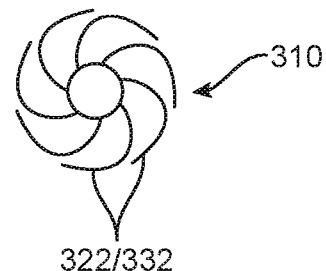
FIG. 3F is a view of a portion of an attachment assembly of a delivery system in accordance with the present technology.

The first and second arms 322 and 332 may extend radially as shown in FIG. 3B. Alternatively, the first and second arms 322 and 332 may extend in spiral arrangement such as with the attachment assembly 310 shown in FIG. 3F. The spiral arrangement of first and second arms 322 and 332 may be more axially flexible when compressed into a delivery catheter than the radial delivery arms shown in FIG. 3B.

Figure 3G:
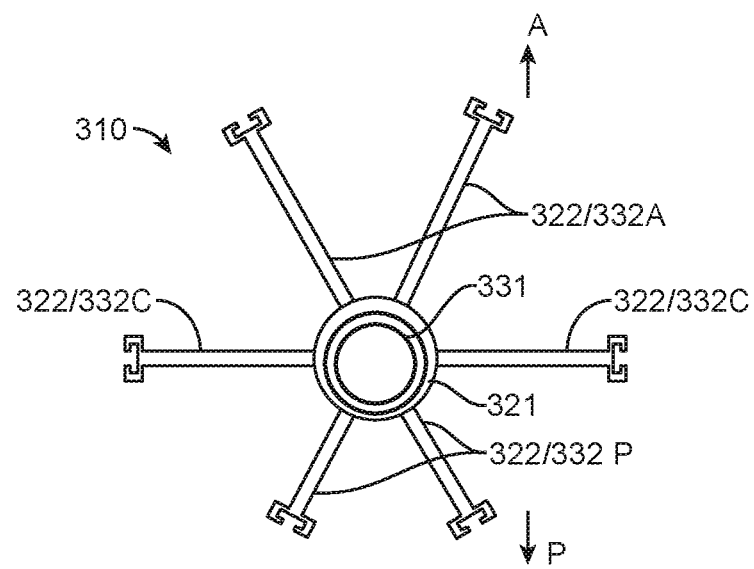
FIG. 3G is a view of an attachment assembly of a delivery system in accordance with the present technology.

The pairs of first and second arms 322 and 332 may all be the same length as shown in FIG. 3C, or the pairs of first and second arm 322 and 332 may have different lengths at different locations around the delivery catheter 302. For example, referring to FIG. 3G, the pairs of first and second arms 322 and 332 on one side may be shorter than the pairs of first and second arms 322 and 332 on another side. In a specific example, the attachment assembly 310 can have anterior arm pairs 322/332A and commissural arm pairs 322/332C that are longer than posterior arm pairs 322/332P. The commissural arm pairs 322/332C can have a length between the lengths of the anterior and posterior arm pairs 322/332A and 322/332P, respectively. If the arm pairs have different lengths, the first and second actuators 321 and 331, respectively, may be offset from the central axis of the valve, i.e., off-centered. For example, it may be preferable to have the first and second actuators 321 and 331, respectively, closer to the posterior leaflet of the native mitral valve to better control the positioning of the implantable device 200. If the arm pairs 322/332 are of different lengths, then as the implantable device 200 is collapsed into the sleeve, the atrial-fixation member 202 may be housed in the sleeve in a skewed orientation, which may allow the diameter of the implantable device 200 to be compressed further.

Although the system 300 is depicted with multiple pairs of first and second arms 322 and 332, a single pair of first and second arms 322 and 332 may suffice. It will be appreciated that the first and second arms 322 and 332 may engage all the chevrons 202V (FIG. 2) described above, or only some of them (e.g., as few as a single chevron 202V). The chevrons 202V that are not attached to an arm pair can be shaped so that when the arms pull the implantable device 200 together into the sleeve, the non-attached chevrons also collapse into the sleeve at the same time.

FIGS. 4A-4F illustrate stages of delivering and deploying an implantable device 200 using an embodiment of the delivery catheter 302 and the attachment assembly 310 along with a steerable guide catheter 410 or series of coaxial guide catheters. Referring to FIG. 4A, the guide catheter 410 can be inserted to traverse the venous system to the right atrium and then across the interatrial septum S into the left atrium LA. In some embodiments, the distal portion of the guide catheter 410 can be positioned so that its distal-most end (e.g., the end furthest from the user) is in the left atrium. For example, the guide catheter 410 can extend to a location as shown in FIG. 4A, or the guide catheter 410 can be positioned further in the left atrium LA to extend at least generally along the flow axis of the native cardiac valve (e.g., a generally vertical axis VA in FIG. 4A). This alignment can be achieved via a combination of torqueing the guide catheter 410, pre-shaping the end of the guide catheter 410, and the steerability features of the guide catheter 410 that configure the end of the guide catheter 410 to be deflected along one or more axes. However, in some embodiments, the guide catheter 410 may not have such complete steerability and its distal tip positioning may be more approximate such that additional positioning via the delivery catheter may be desired.

One optional steerability feature of the delivery catheter 302 is that it can be torqued to rotate the implantable device 200 for alignment with specific locations of the cardiac valve. Another optional steerability feature of the delivery catheter 302 adjusts the angle of the implantable device 200 to be angled with respect to the tip of the delivery catheter 302 (longitudinal axis). Various embodiments of such an angular steerability feature are described below with respect to FIGS. 11A-13. The delivery system can also have a cover sleeve (not shown) positioned coaxially over the delivery catheter 302 and inside the guide catheter 410. The cover sleeve can be advanced over the implantable device 200 to collapse the implantable device 200 for delivery, repositioning, and retrieval if desired. The cover sleeve may also be deflectable in one or more directions. Features such as a duck billed hemostasis valve can be incorporated at the proximal end of the guide catheter 410 to maintain hemostasis during and after introduction of the cover sleeve.

Referring to FIG. 4B, the guide catheter 410 can be placed through the atrial septum S via a trans-femoral approach (or through the atrial roof in a trans-atrial approach). The steerable guide catheter 410 may be deflectable in one or more directions and can be advanced through the septum toward the mitral valve to facilitate optimal positioning of the implantable device 200. The delivery catheter 302 can then be advanced through the steerable guide catheter 410 and into the left atrium LA.

Referring to FIG. 4C, the arm pairs 322/332 are at least partially unsheathed such that they are positioned distally from the sheath of the delivery catheter 302 within the atrium. At this point, the atrial-fixation member 202 is partially expanded and a clip 220 coupled to the baffle 214 is exposed.

Referring to FIG. 4D, the implantable device 200 can be oriented as desired by rotating the delivery catheter 302 within a cover sleeve of the delivery catheter 302, rotating the cover sleeve within the guide catheter 410, steering the cover sleeve and/or guide catheter 410, and/or pulling/pushing control wires (not shown). As further shown in FIG. 4D, the clip 220 coupled to the baffle 214 can be opened and positioned to capture the posterior leaflet between the clip 220 and the baffle 214. When the implantable device 200 is rotationally and radially aligned, it can be advanced to the desired axial position within the native mitral valve. The clip 220 can be closed once it is positioned under the desired native leaflet. Cinching sutures (not shown) may be used to control the expansion of the atrial-fixation member 202 once it is positioned within the mitral valve. Alternatively, further unsheathing of the first and second arms 322 and 332 may provide a controlled final expansion of the implantable device 200 independent of cinching sutures.

FIG. 4E shows the process after the implantable device 200 has been fully expanded and the clip 220 has clamped the native leaflet to the baffle 214. The performance of the implantable device 200 can then be evaluated via TEE echo imaging, and the implantable device 200 can be released, repositioned, or re-sheathed and removed. If the implantable device 200 is ready to be released, the cinch lines can be released and withdrawn through the delivery catheter 302.

FIG. 4F shows the process after the attachment assembly 310 (FIGS. 3A-3G) has been actuated such that the connectors 205 of the implantable device 200 have detached from the connectors 324 of the attachment assembly 310. The delivery catheter 302 can then be removed through the guide catheter 410, and then the guide catheter 410 can be withdrawn from the patient.

Figure 5A:
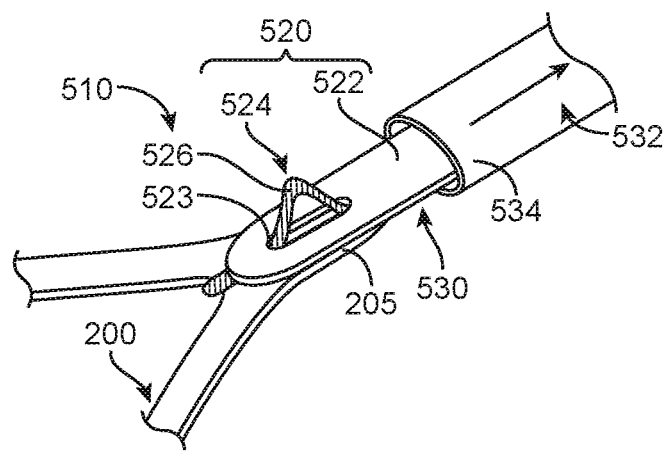
FIGS. 5A and 5B depict a portion of an attachment assembly for attaching the delivery system to an implantable device.
Figure 5B:
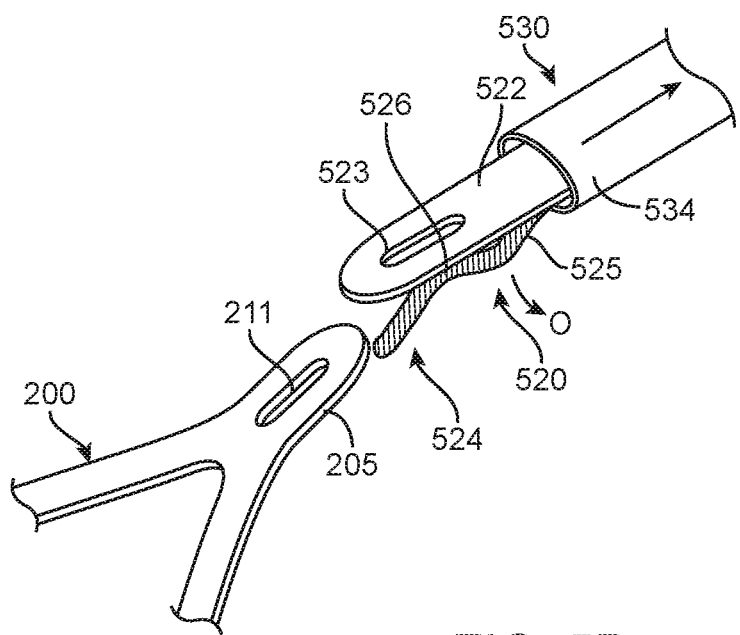

FIG. 5A is an isometric view of an attachment assembly 510 shown in a locked position and FIG. 5B is an isometric view of the attachment assembly 510 in a released position in accordance with the present technology. The attachment assembly 510 may be used in place of the attachment assembly 310 described above. The attachment assembly 510 includes a connector mechanism 520 having a first arm 522, an opening 523 in the first arm, and a connector 524. The connector 524 can be a spring wire having a base 525 (FIG. 5B) and a latch 526. The attachment assembly 510 can further include a locking mechanism 530 having a second arm 532 with a retainer 534. The second arm 532 can be a tube, and the retainer 534 can be a distal portion of the tube. The first arm 522 of the connector assembly 520 can extend through a lumen of the second arm 532.

In the locked position shown in FIG. 5A, the second arm 532 covers the base 525 of the connector 524 such that the latch 526 is positioned through (a) a hole 211 in the connector 205 of the implantable device 200 and (b) the opening 523 at the distal portion of the first arm 522. The latch 526 accordingly secures the connector 205 to the first arm 522 in the locked position. To move the attachment assembly 510 into the open position shown in FIG. 5B, the first arm 522 is moved distally and/or the second arm 532 is moved proximally such that at least a portion of the base 525 of the connector 524 is free of the retainer 534. The connector 524 can be formed from stainless steel, Nickel-Titanium alloys, or other suitable materials such that the base 525 moves the connector 524 to an open position (Arrow O) in which the latch 526 can disengage the opening 523 and the hole 211. The connector 205 can then be disengaged from the connector mechanism 520 to deploy the implantable device 200.

Figure 6A:
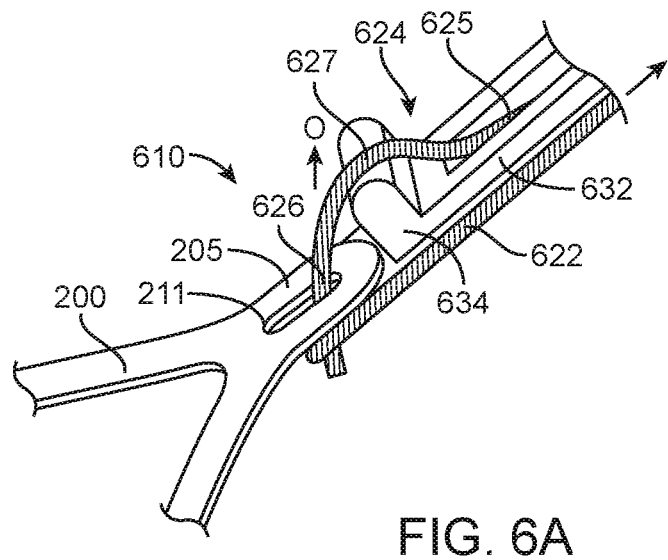
FIGS. 6A and 6B depict a portion of an attachment assembly for attaching the delivery system to an implantable device.
Figure 6B:
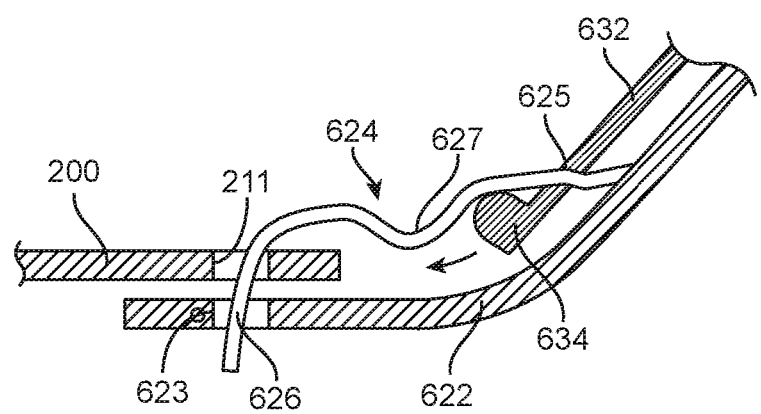

FIGS. 6A and 6B depict an attachment assembly 610 which may be used in place of the attachment assemblies 310 and 510 described above. The attachment assembly 610 can include a connector mechanism having a first arm 622, an opening 623 through a distal portion of the first arm 622, and a connector 624 attached to the first arm 622. The connector 624 can include a base 625 attached to the first arm 622, a latch 626 configured to be received through the hole 211 of the implantable device 200 and the opening 623 in the locked position, and a detent 627 between the base 625 and the latch 626. The attachment assembly 610 can further include a locking mechanism having a second arm 632 and a driver 634. The second arm 632 can have a slot 626 in which the base 625 of the connector 624 is received. In the embodiment shown in FIG. 6A, the latch 626 is removed from the hole 211 and the opening 623 by moving the second arm 632 distally so that the driver 634 engages the detent 627 and moves the connector 624 outwardly.

Figure 7:
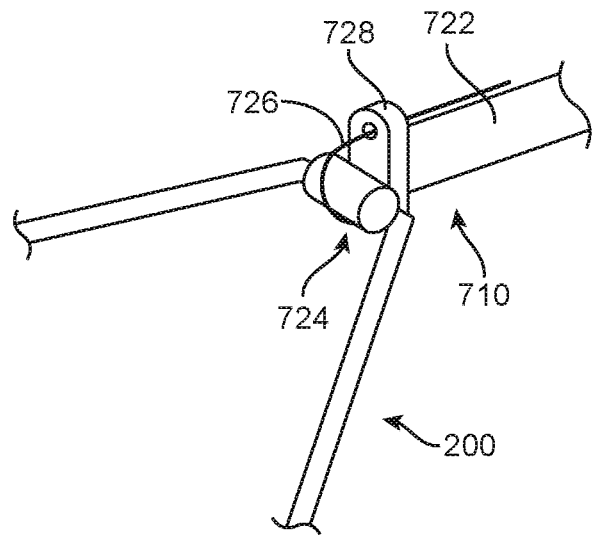
FIG. 7 depicts a portion of an attachment assembly for attaching the delivery system to an implantable device.

FIG. 7 shows an attachment assembly 710 which may be used in place of the attachment assemblies 310, 510 and 610 described above. The attachment assembly 710 includes an arm 722 and a connector 724. The connector 724 can be a helically wound lock suture, cable, or wire 726. A proximal end of the wire 726 is attached to an actuator outside the body, and the wire 726 extends along the arm 722 and through an eyelet 728 or the like at the distal of the arm 722. The distal end of the wire 726 is wrapped around a portion of the implantable device 200 several times thereby securing the implant 200 to the delivery system 300. The implantable device 200 is disengaged from the delivery system 300 by retracting the wire 726, which unspools the wire from engagement with the implant 200. The wire 726 may be formed of surgical grade stainless steel or a Nickel-Titanium alloy, such as Nitinol® or the like, which is pre-formed to a coil shape. If just one coil of the wire 726 is passed through the eyelet 728 and wrapped around implant 200, the forces between the arm 722 and the implantable device 200 could potentially uncoil the wire 726 causing the two parts to prematurely separate. However, the implantable device 200 is better retained with multiple coils of the wire 726 passing through both the arm 722 and the implantable device 200.

Figure 8:
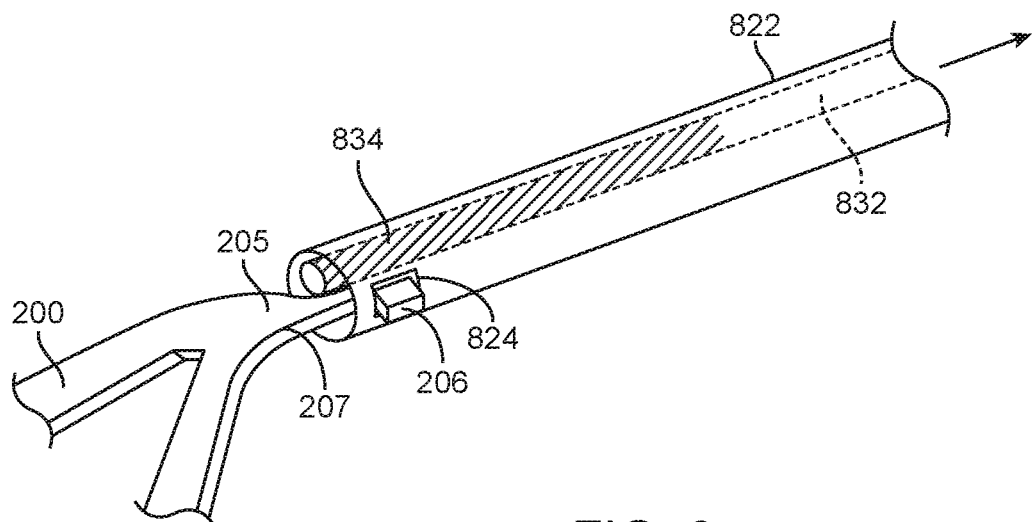
FIG. 8 depicts a portion of an attachment assembly for attaching the delivery system to an implantable device.

FIG. 8 depicts one arm pair of another attachment assembly 810 in accordance with the present technology. The attachment assembly 810 includes a connector mechanism having a first arm 822 with a connector 824, and a locking mechanism having a second arm 832 with a retainer 834. The first arm 822 can be a tube and the connector 824 can be an opening at the distal end of the first arm 822. The second arm 832 can be a wire and the retainer 834 can be a distal portion of the wire. The connector 205 of the implantable device 200 has a head 206 configured to be received in the connector 824 and a neck 207 extending along the retainer 834 in the locked position. In operation the first arm 822 and/or the second arm 832 are moved such that the retainer 834 is positioned proximal of the head 206. The head 206 can then disengage the connector 824 to release the implantable device 200 from the attachment assembly 810. The connector 205 and the connector 824 may be formed of a resilient metal or plastic material including a super-elastic Nickel-Titanium alloy (Nitinol®). The arm pair shown in FIG. 8 is a single arm pair, and it will be appreciated that the attachment assembly 810 can have two or more arm pairs (e.g., 2, 3, 4, 5, 6, 7, 8 or more) as shown above in FIG. 3B, 3F or 3G.

Figure 9C:
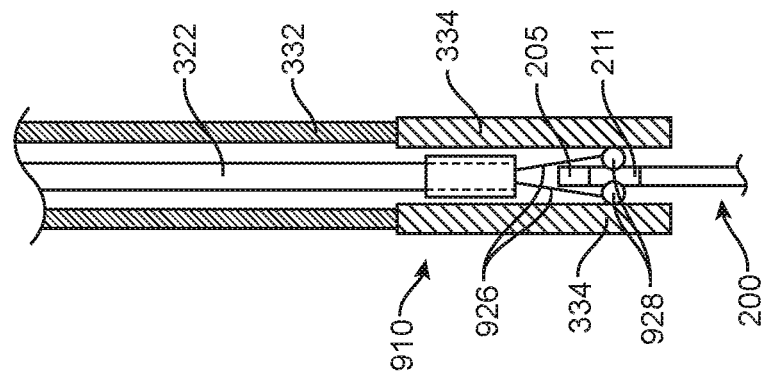
FIGS. 9A-9C depict a connector mechanism and locking mechanism for attaching the delivery system to an implantable device.
Figure 9B:
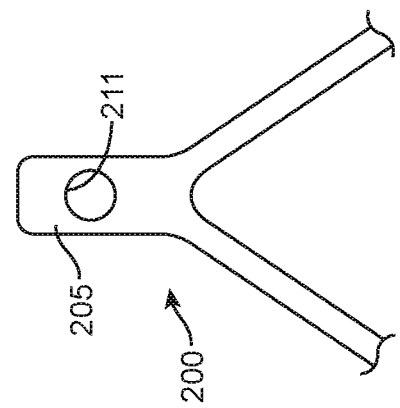
Figure 9A:
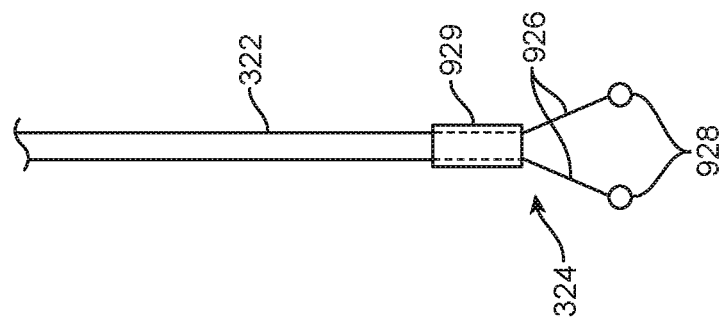

FIG. 9A shows a connector mechanism having a first arm 322 and a connector 324 in accordance with an embodiment of the technology, and FIG. 9B shows a connector 205 of the implantable device 200 for use with the connector 324 of FIG. 9A. Referring to FIG. 9A, the connector 324 has fingers 926 extending from the distal portion of the first arm 322 and a ball 928 at the end of each finger 926. The fingers 926 can be flexible wires, such as stainless steel or Nitinol®, and the proximal end of the fingers 926 can be attached to the first arm 322 by a hub 929. The connector 205 of the implantable device 200 can include a hole 211 (FIG. 9B).

FIG. 9C shows one arm pair of an attachment assembly 910 having (a) a locking mechanism including a second arm 332 and a retainer 334 defined by a distal portion of the second arm 332, and (b) the connector mechanism shown in FIG. 9B. The arm pair 322/332 shown in FIG. 9C is a single arm pair, and it will be appreciated that the attachment assembly 910 can have two or more arm pairs (e.g., 2, 3, 4, 5, 6, 7, 8 or more) arranged as shown above in FIG. 3B, 3F or 3G.

FIG. 9C shows the attachment assembly 910 in a locked position in which the connector 324 (FIG. 9A) is within retainer 334 while the balls 928 are positioned in the hole 211 of the connector 205. The retainer 334 accordingly holds the balls 928 in the hole 211 to lock the implantable device 200 (FIG. 2) to the attachment assembly 910. The implantable device 200 is released from the connector 324 by moving the first arm 322 distally and/or moving the second arm 332 proximally such that the retainer 334 disengages the balls 928. At this point, the fingers 926 can optionally spread apart from each other via an inherent spring force in the fingers 926 to disengage the balls 928 from the hole 211.

Figure 10A:
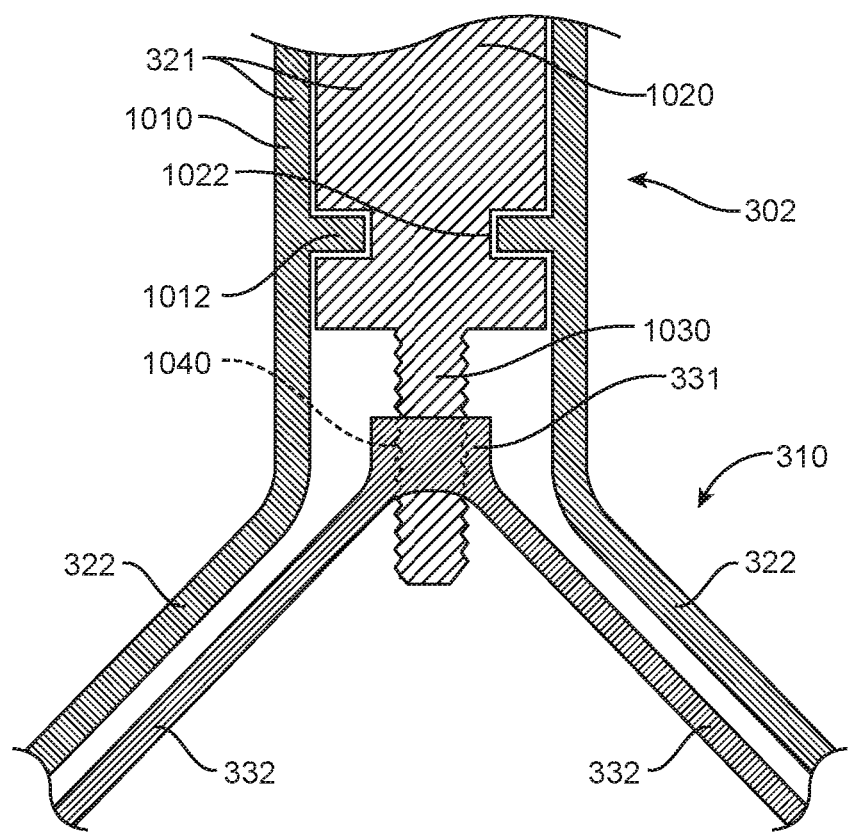
FIG. 10A is a detailed view of an attachment assembly in accordance with the present technology.

FIG. 10A is a detailed cross-sectional view of an attachment assembly 310 in accordance with the present technology. The attachment assembly 310 has first and second arms 322 and 332 as described above. The first actuator 321 includes a first tube 1010 having a holder 1012 and a driver 1020 having a guide 1022, and the holder 1012 and guide 1022 are arranged such that the holder 1012 is received in the guide 1022. The driver 1020 further includes a threaded shaft 1030. The second actuator 331 is a threaded bore 1040 engaged with the threaded shaft 1030. In operation, the driver 1020 rotates one direction to move the second actuator 331 along the threaded shaft 1030, which in turn moves the second arms 332 along the first arms 322 to move the retainer 334 with respect to the connector 324 (FIGS. 3B and 3C).

Figure 10B:
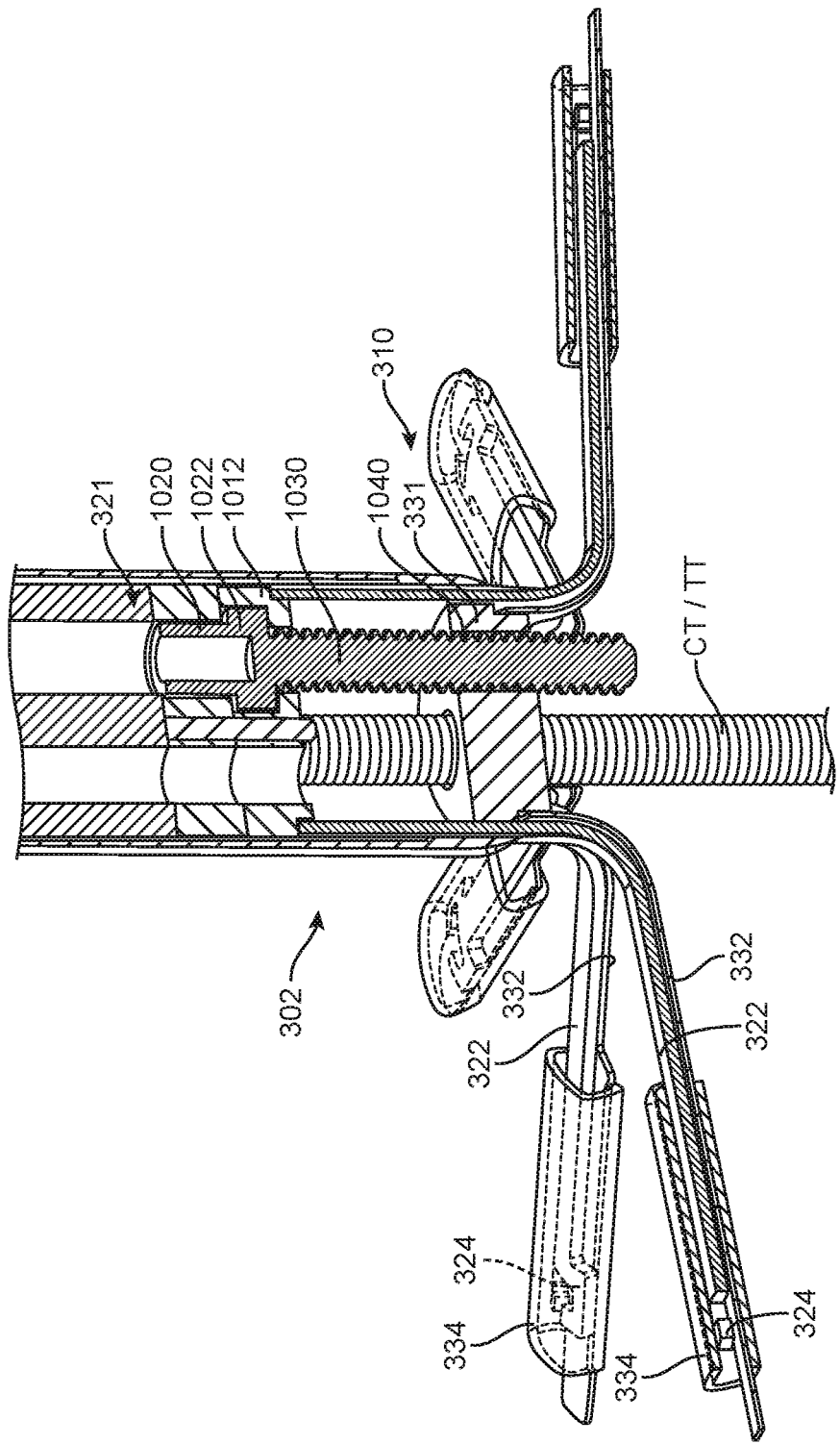
FIG. 10B is a detailed view of an attachment assembly in accordance with the present technology.

FIG. 10B is a detailed cross-sectional view of an attachment assembly 310 in accordance with the present technology. The attachment assembly 310 shown in FIG. 10B has a first actuator 321 including a holder 1012 defined by a channel and a guide 1022 defined by a shoulder such that the guide 1022 is received in the holder 1012. The attachment assembly 310 shown in FIG. 10B also includes a driver 1020 coupled to a threaded shaft 1030 and a second actuator 331 having a threaded bore 1040 engaged with the threaded shaft 1030. The attachment assembly 310 shown in FIG. 10B operates analogously to the attachment assembly 310 shown in FIG. 10A. Additionally, FIG. 10B shows a cinch tube CT or tendon tube TT that houses the suture lines for cinching the implantable device during delivery. The cinch tube CT or tendon tube TT can be a coiled tube.

Figure 11A:
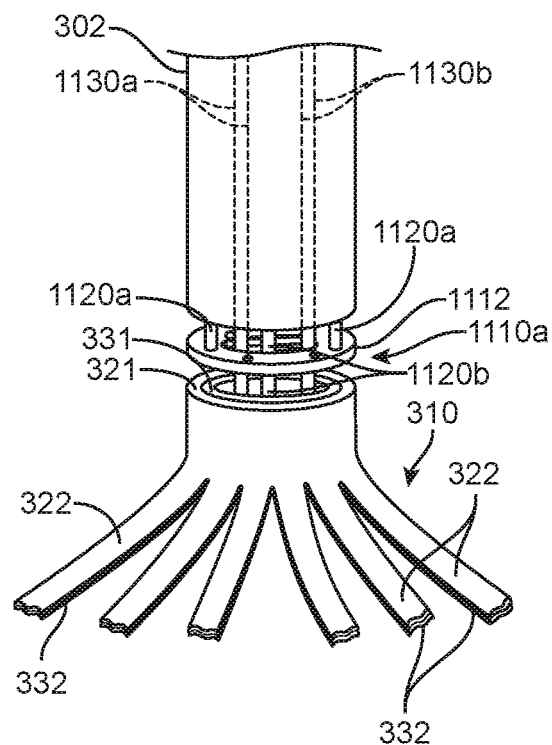
FIGS. 11A-11C depict universal joint mechanisms for enabling tilt control of an attachment assembly.
Figure 11B:
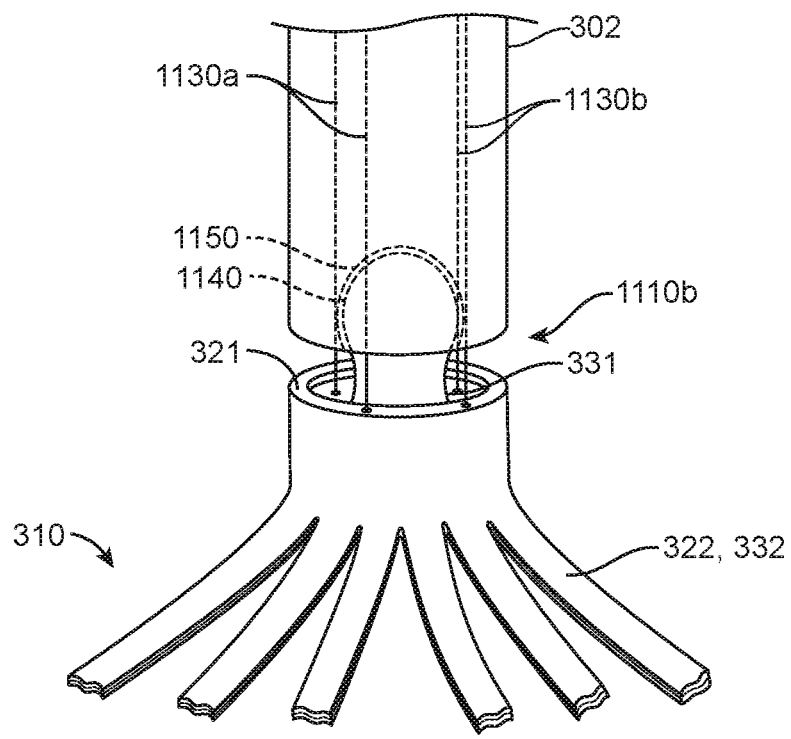
Figure 11C:
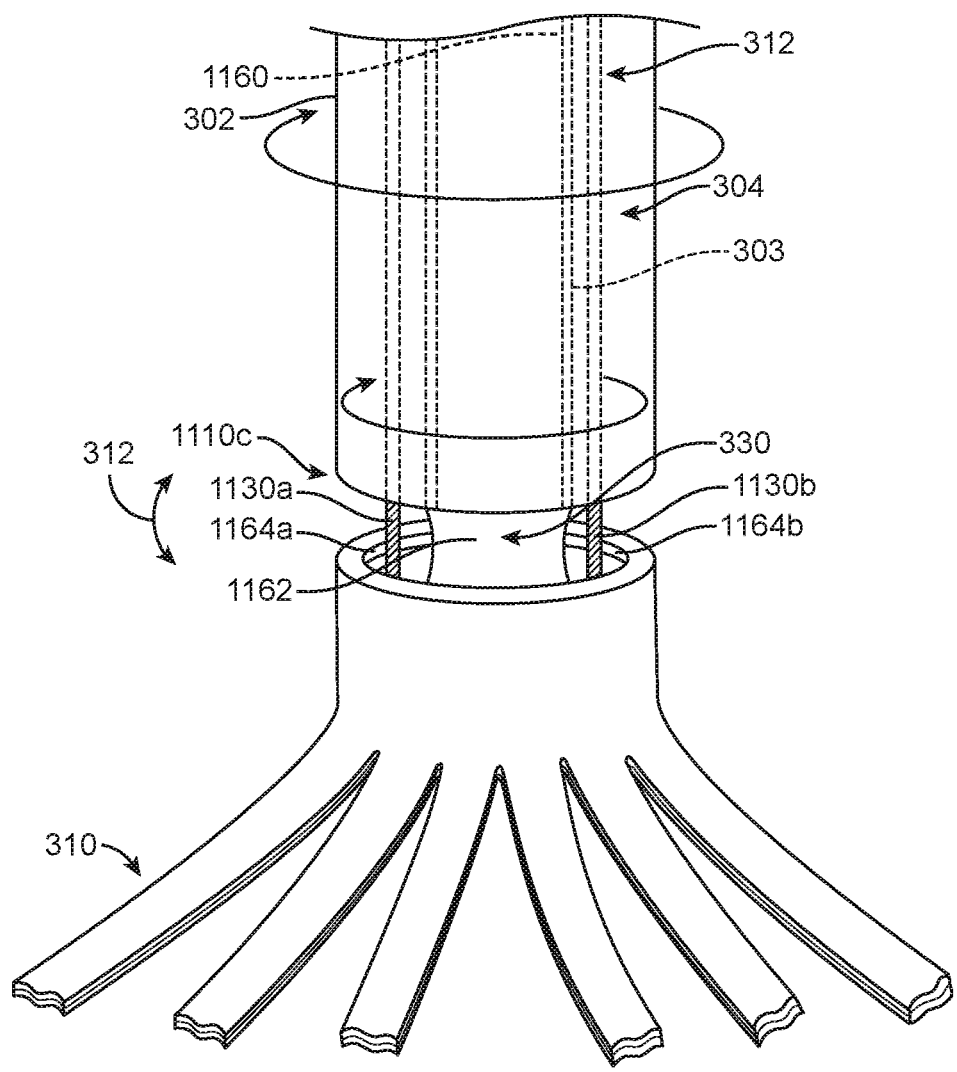

FIGS. 11A-11C are enlarged views of universal joints in accordance with the present technology that are configured to steer the attachment assembly in multiple directions. Like reference numbers refer to like components in FIGS. 11A-11O. FIG. 11A shows an example universal joint 1110a which includes a spacer 1112, first hinges 1120a, second hinges 1120b, first control wires 1130a, and second control wires 1130b. The first and second hinges 1120a and 1120b can be flexible posts made from a metal (e.g., stainless steel or Nickel-Titanium alloy such as Nitinol®). The first hinges 1120a connect the spacer 1112 to the delivery catheter 302, and the second hinges 1120b connect the spacer 1112 to the attachment assembly 310. The first and second hinges 1120a and 1120b can be offset from each other relative to the circumference of the spacer. For example, the first and second hinges 1120a and 1120b can be offset by 180 degrees or another suitable orientation. The spacer 1112 can have holes 1114 through which the first and second control wires 1130a and 1130b pass. The first control wires 1130a can be attached to the first actuator 321 and the second control wires 1130b can be attached to the second actuator 331. The control wires 1130a and 1130b may also extend through a central lumen of the delivery catheter 302 or through one or more auxiliary lumens formed in the sidewall of the delivery catheter 302. The control wires 1130a and 1130b may be flexible or rigid such that they may be pushed and/or pulled to transmit steering forces to the attachment assembly 310.

In operation, the first and second control wires 1130a and 1130b can be manipulated to change the angular orientation of the attachment assembly 310. For example, the first and second control wires 1030a and 1030b can be pulled/pushed so that the attachment assembly 310 pivots with respect to the spacer 1012.

FIG. 11B shows an example universal joint 1110b including a ball 1140 and a socket 1150 which cooperatively form a ball-socket joint. The ball 1140 is attached to the second actuator 322 and the socket 1150 is attached to, or integrally formed with, the delivery catheter 302. The delivery catheter 302 can include a central lumen, and the socket 1150 can be an enlarged portion of the central lumen that is slightly larger than the ball 1140. The control wires 1130a and 1130a can extend through the delivery catheter 302, such as through one or more auxiliary lumens formed in the sidewall of the delivery catheter 302. The ball-socket universal joint 1110b allows the attachment assembly 310 to tilt relative to the longitudinal axis of the delivery catheter 302 while enabling the delivery catheter 302 to torque the attachment assembly 310. The first and second arms 322 and 332 are re-oriented by torqueing the delivery catheter 302 and by pulling/pushing on one or more of the control wires 1130a and 1130b.

FIG. 11C shows an example universal joint 1110c including a flexible inner shaft 1160 attached to or integrally formed with the attachment assembly 310 at a flexible joint 1162. The flexible inner shaft 1160 can be coaxially received in a central lumen 303 of the delivery catheter 302. The universal joint 1110c can further include at least two control wires 1130a and 1130b having distal ends slideably received in arcuate slots 1164a and 1164b, respectively, formed in the attachment assembly 310. The control wires 1130a and 1130b extend through the delivery catheter 302 to an actuator outside of the patient (not illustrated). The arcuate slots 1164a and 1164b allow the control wires 1130a and 1130b to move relative to the inner shaft 1160 so the steering direction can remain constant even when the distal tip is rotated.

The control wires 1130a and 1130b may extend through one or more lumens formed in the sidewall of the delivery catheter 302. The control wires 1130a and 1130b may be flexible or rigid such that a pushing force may be transmitted to the attachment assembly 310. In operation, the attachment assembly 310 is orientated to a desired position by torqueing the inner shaft 1160 and by pulling/pushing on one or more of the control wires 1130a and 1130b.

Figure 12:
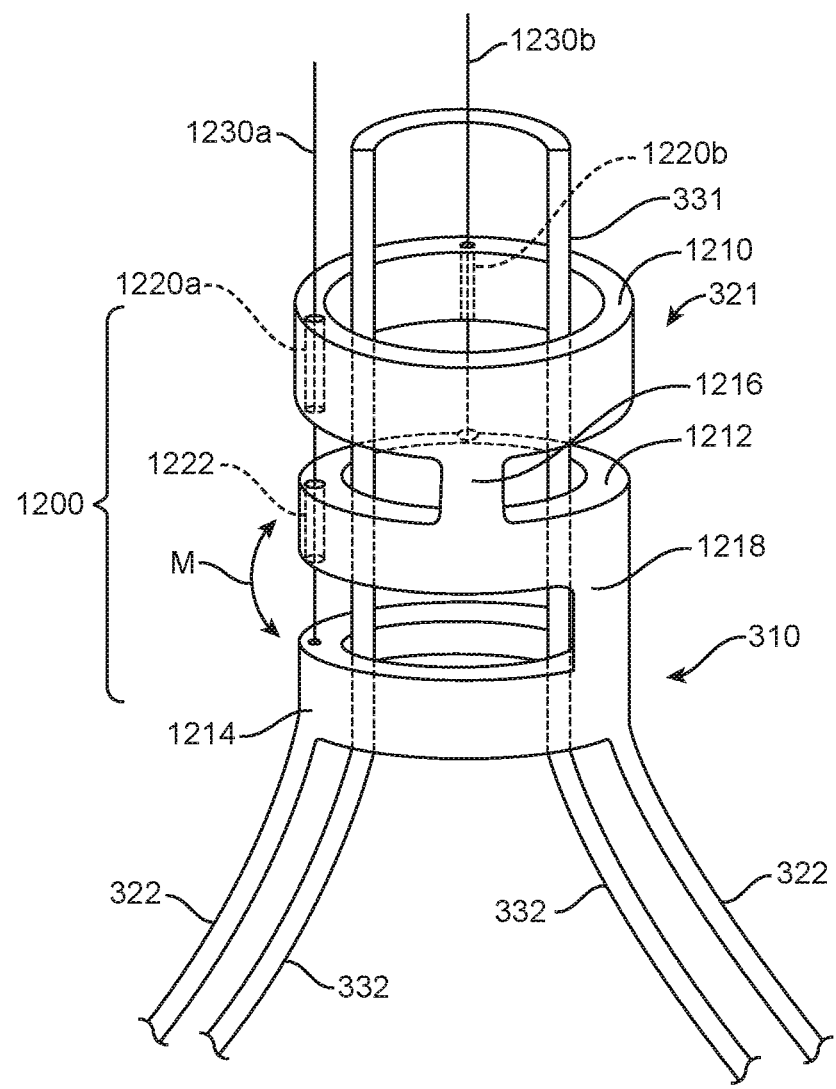
FIG. 12 is a detailed view of an attachment assembly in accordance with the present technology.

FIG. 12 is a detailed view of an attachment assembly 310 in accordance with the present technology. The attachment assembly 310 shown in FIG. 12 has a universal joint 1200 that defines a portion of the first actuator 321. The universal joint 1200 has a first band 1210, a second band 1212, and a third band 1214. In the illustrated embodiment, the first band 1210 is an upper band that can be at a distal portion of an outer tube, the third band 1214 is a lower band from which the first arms 322 can extend, and the second band 1212 is a middle band between the first and third bands 1210 and 1214. The universal joint 1200 further includes a first flexible joint 1216 between the first band 1210 and the second band 1212 and a second flexible joint 1218 between the second band 1212 and the third band 1214. The first and second flexible joints 1216 and 1218 are offset relative to each other by an amount, such as 30°, 45°, 60°, 75°, 90°, 105°, 120°, 135° or 150°. In many cases, the first and second flexible joints 1216 and 1218 can be offset from each by 90° as shown in FIG. 12. The first band 1210 can have first through holes 1220a and 1220b, and the second band 1212 can have a through hole 1222. The attachment assembly 310 can further include a control wire 1230a and a control wire 1230b. The control wire 1230a passes through the holes 1220a and 1222 and is attached to the third band 1214 opposite the second flexible joint 1218. The control wire 1230b passes through the through hole 1220a and is attached to the second band 1212 opposite the first flexible joint 1216. The attachment assembly 310 can also include a second actuator 331 defined by a tube that passes through the universal joint 1200 and second arms 332 that extend from the second actuator 331.

In operation, the attachment assembly 310 can be angularly orientated by manipulating the control wires 1230a and 1230b. For example, the control wire 1230a can be pulled/pushed such that second flexible joint 1218 bends and the third band 1214 moves in a plane of the second flexible joint 1218 (shown by arrow M in FIG. 12), and/or the control wire 1230b can be pulled/pushed such that the first flexible joint 1216 bends and the second band 1212 moves in a plane of the first flexible joint 1216 (orthogonal to the plane of arrow M). This allows an operator to angularly position the attachment assembly 310 while the implantable device 200 is proximate the heart valve.

Figure 13:
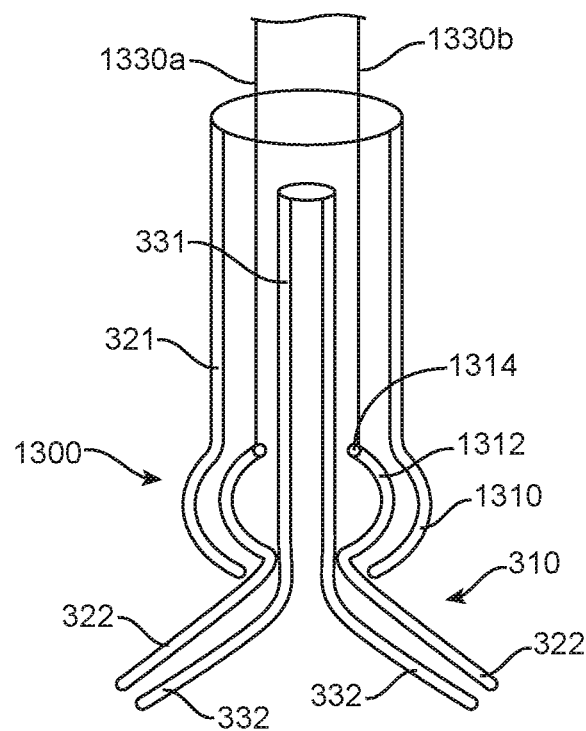
FIG. 13 is a detailed view of an attachment assembly in accordance with the present technology.

FIG. 13 is a detailed view of an attachment assembly 310 in accordance with the present technology. The attachment assembly 310 shown in FIG. 13 has a ball-type universal joint 1300 that defines a portion of the first actuator 321. The universal joint 1300 can include a cup 1310, a ball 1312 configured to be rotatably contained by the cup 1310, and an opening 1314 through the ball 1312. The cup 1310 can be a distal portion of an outer tube that defines the first actuator 321, and the ball 1312 can define a hub from which the first arms 322 extend. The second actuator 331 can extend through the opening 1314 of the ball 1312, and the second arms 332 can extend from the second actuator 331. In operation, one or both of the first and second actuators 321/331 can be pushed/pulled to move the first and/or second arms 322/332 relative to each other to release implantable device from the attachment assembly 310. The angular orientation of the ball 1312 with respect to the cup 1310 can be controlled using one or more control wires 1330a and/or 1330b at different circumferential locations of the ball 1312.

In any of the examples disclosed herein, the control wires 1030a/b, 1130a/b, 1230a/b and 1330a/b (collectively "control wires") may be a rod, a cable (braided wire), or wire. The control wires may be attached to or integrally formed with the attachment assembly 310. The control wires may be formed of a biocompatible material such as surgical grade stainless steel or a super elastic Nickel-Titanium alloy such as Nitinol®.

EXAMPLES

Various examples of aspects of the subject technology described above with reference to FIGS. 3A-13 are provided as numbered clauses (1, 2, 3, etc.) for convenience. These are provided as examples and do not limit the subject technology.

1. A delivery system for implanting a medical device, comprising:
   a delivery catheter having a proximal portion and a distal portion;
   a connector mechanism having first arms and connectors, each first arm has a proximal portion coupled to the delivery catheter and a distal portion, and each connector is at the distal portion of a corresponding first arm and configured to engage the medical device;
   a locking mechanism having second arms and retainers, each second arm has a proximal portion coupled to the delivery catheter and a distal portion, and each retainer is at the distal portion of a corresponding second arm and configured to maintain engagement between the connector and the medical device in a locked position; and
   wherein each first arm is associated with a corresponding second arm to define pairs of first and second arms in which the first arm and/or the second arm move relative to each other to a released position in which the retainer of the second arm is moved from the connector of the corresponding first arm to release the medical device.

2. The delivery system of clause 1 wherein the delivery catheter has a first actuator and a second actuator, and wherein the first arms are coupled to the first actuator, the second arms are coupled to the second actuator, and the first actuator and/or second actuator can move relative to the other.

3. The delivery system of any of clauses 1-2 wherein the connector mechanism has at least 3 first arms and the locking mechanism has at least 3 second arms.

4. The delivery system of any of clauses 1-3 wherein the first arms and the second arms are substantially straight.

5. The delivery system of any of clauses 1-3 wherein the first arms and the second arms are curved.

6. The delivery system of any of clauses 1-5 wherein the connectors have fingers configured into a C-shape and the retainers are sleeves that fit over the C-shaped fingers in the locked position.

7. The delivery system of any of clauses 1-5 wherein the connectors having a head and a neck, and the retainers are sleeves that fit over the heads in the locked position.

8. The delivery system of any of clauses 1-5 wherein each first arm has an opening and the connectors are spring wires, and each spring wire has a base coupled to a corresponding first arm and a latch configured to be in the opening in the locked position.

9. The delivery system of any of clauses 1-5 wherein each first arm is a tube and the connector is an opening at a distal portion of the tube, and each second arm is a rod within the tube and the retainer is a distal portion of the rod.

10. The delivery system of any of clauses 1-5 wherein each connector comprises at least one flexible finger and a ball attached to the finger, and each second arm comprises a tube with the retainer comprising a distal portion of the tube.

11. The delivery system of any of clauses 1-10, further comprising a universal joint between the delivery catheter and the first and second arms.

12. The delivery catheter of any of clauses 11 wherein the universal joint has a plurality of control wires, a spacer between the delivery catheter and the first and second arms, and flexible hinges coupling one side of the spacer to the delivery catheter and another side of the spacer to the first and second arms.

13. The delivery system of any of clauses 12 wherein the flexible hinges include a first set of hinges coupling the one side of the spacer to the delivery catheter and a second set of hinges coupling the other side of the spacer to the first and second arms, and wherein the first set of hinges are circumferentially offset from the second set of hinges.

14. The delivery system of any of clauses 11 wherein the universal joint has a ball coupled to the first and second arm and a socket in the delivery catheter configured to receive the ball.

15. The delivery system of any of clauses 11 wherein the universal joint has a flexible inner shaft coupled to the first and second arms and control wires.

16. A delivery system for placing an implantable device, comprising:
   a delivery catheter having a proximal portion and a distal portion; and
   an attachment assembly having arm pairs in which individual arm pairs include a first arm with connector and a second arm with a retainer, wherein (a) each first arm extends along a corresponding second arm, and (b) the first arm and/or the second arm moves relative to the other from a locked position in which the retainer interfaces with the connector to maintain engagement between the implantable device and the connector to a released position in which the retainer is positioned relative to the connector such that the implantable device can disengage the connector.

17. The delivery system of clause 16 wherein the connector mechanism has at least 3 first arms and the locking mechanism has at least 3 second arms.

18. The delivery system of any of clauses 16-17 wherein the first arms and the second arms are substantially straight.

19. The delivery system of any of clauses 16-17 wherein the first arms and the second arms are curved.

20. The delivery system of any of clauses 16-19 wherein the connectors have fingers configured into a C-shape and the retainers are sleeves that fit over the C-shaped fingers in the locked position.

21. The delivery system of any of clauses 16-19 wherein the connectors having a head and a neck, and the retainers are sleeves that fit over the heads in the locked position.

22. The delivery system of any of clauses 16-19 wherein each first arm has an opening and the connectors are spring wires, and each spring wire has a base coupled to a corresponding first arm and a latch configured to be in the opening in the locked position.

23. The delivery system of any of clauses 16-19 wherein each first arm is a tube and the connector is an opening at a distal portion of the tube, and each second arm is a rod within the tube and the retainer is a distal portion of the rod.

24. The delivery system of any of clauses 16-19 wherein each connector comprises at least one flexible finger and a ball attached to the finger, and each second arm comprises a tube with the retainer comprising a distal portion of the tube.

25. The delivery system of any of clauses 16-24, further comprising a universal joint between the delivery catheter and the first and second arms.

26. The delivery catheter of any of clauses 25 wherein the universal joint has a plurality of control wires, a spacer between the delivery catheter and the first and second arms, and flexible hinges coupling one side of the spacer to the delivery catheter and another side of the spacer to the first and second arms.

27. The delivery system of any of clauses 26 wherein the flexible hinges include a first set of hinges coupling the one side of the spacer to the delivery catheter and a second set of hinges coupling the other side of the spacer to the first and second arms, and wherein the first set of hinges are circumferentially offset from the second set of hinges.

28. The delivery system of any of clauses 25 wherein the universal joint has a ball coupled to the first and second arm and a socket in the delivery catheter configured to receive the ball.

29. The delivery system of any of clauses 25 wherein the universal joint has a flexible inner shaft coupled to the first and second arms and control wires.

30. The delivery system of any of clauses 1-29 wherein the delivery catheter has a first actuator and a second actuator, and wherein the first arms are coupled to the first actuator, the second arms are coupled to the second actuator, and the first actuator and/or second actuator can move relative to the other.

From the foregoing, it will be appreciated that specific embodiments of the technology have been described herein for purposes of illustration, but that various modifications may be made without deviating from the disclosure. Accordingly, the invention is not limited except as by the appended claims. Furthermore, certain aspects of the new technology described in the context of particular embodiments may also be combined or eliminated in other embodiments. For example, instead of the mechanical connection mechanisms and locking mechanism described above, the attachment assemblies can have electrolytic detachment mechanisms at the end of each first arm. Moreover, although advantages associated with certain embodiments of the new technology have been described in the context of those embodiments, other embodiments may also exhibit such advantages and not all embodiments need necessarily exhibit such advantages to fall within the scope of the technology. Accordingly, the disclosure and associated technology can encompass other embodiments not expressly shown or described herein.

We claim:

1. A delivery system for implanting a medical device, comprising:
   a delivery catheter having a proximal portion and a distal portion;
   a connector mechanism having first arms and connectors, each first arm has a proximal portion coupled to the delivery catheter and a distal portion, and each connector is at the distal portion of a corresponding first arm and configured to engage the medical device;
   a locking mechanism having second arms and retainers, each second arm has a proximal portion coupled to the delivery catheter and a distal portion, and each retainer is at the distal portion of a corresponding second arm and configured to maintain engagement between the connector and the medical device in a locked position; and
   a universal joint between the delivery catheter and the first and second arms,
   wherein each first arm is associated with a corresponding second arm to define pairs of first and second arms in which the first arm and/or the second arm move relative to each other to a released position in which the retainer of the second arm is moved from the connector of the corresponding first arm to release the medical device.

2. The delivery system of claim 1 wherein the delivery catheter has a first actuator and a second actuator, and wherein the first arms are coupled to the first actuator, the second arms are coupled to the second actuator, and the first actuator and/or second actuator can move relative to the other.

3. The delivery system of claim 1 wherein the connector mechanism has at least 3 first arms and the locking mechanism has at least 3 second arms.

4. The delivery system of claim 1 wherein the first arms and the second arms are straight.

5. The delivery system of claim 1 wherein the first arms and the second arms are curved.

6. The delivery system of claim 1 wherein the connectors have fingers configured into a C-shape and the retainers are sleeves that fit over the C-shaped fingers in the locked position.

7. The delivery system of claim 1 wherein the connectors having a head and a neck, and the retainers are sleeves that fit over the heads in the locked position.

8. The delivery system of claim 1 wherein each first arm has an opening and the connectors are spring wires, and each spring wire has a base coupled to a corresponding first arm and a latch configured to be in the opening in the locked position.

9. The delivery system of claim 1 wherein each first arm is a tube and the connector is an opening at a distal portion of the tube, and each second arm is a rod within the tube and the retainer is a distal portion of the rod.

10. The delivery system of claim 1 wherein each connector comprises at least one flexible finger and a ball attached to the finger, and each second arm comprises a tube with the retainer comprising a distal portion of the tube.

11. The delivery catheter of claim 1 wherein the universal joint has a plurality of control wires, a spacer between the delivery catheter and the first and second arms, and flexible hinges coupling one side of the spacer to the delivery catheter and another side of the spacer to the first and second arms.

12. The delivery system of claim 11 wherein the flexible hinges include a first set of hinges coupling the one side of the spacer to the delivery catheter and a second set of hinges coupling the other side of the spacer to the first and second arms, and wherein the first set of hinges are circumferentially offset from the second set of hinges.

13. The delivery system of claim 1 wherein the universal joint has a ball coupled to the first and second arm and a socket in the delivery catheter configured to receive the ball.

14. The delivery system of claim 1 wherein the universal joint has (i) a flexible inner shaft coupled to the first and second arms and (ii) control wires.

15. A delivery system for placing an implantable device, comprising:
   a delivery catheter having a proximal portion and a distal portion;
   an attachment assembly having arm pairs in which individual arm pairs include a first arm with a connector and a second arm with a retainer, wherein (a) each first arm extends along a corresponding second arm, and (b) the first arm and/or the second arm moves relative to the other from a locked position in which the retainer interfaces with the connector to maintain engagement between the implantable device and the connector to a released position in which the retainer is positioned relative to the connector such that the implantable device can disengage the connector; and
   a universal joint between the delivery catheter and the first and second arms.

16. The delivery system of claim 15 wherein the delivery catheter has a first actuator and a second actuator, and wherein the first arms are coupled to the first actuator, the second arms are coupled to the second actuator, and the first actuator and/or second actuator can move relative to the other.

17. The delivery system of claim 15 wherein the connector mechanism has at least 3 first arms and the locking mechanism has at least 3 second arms.

18. The delivery system of claim 15 wherein the first arms and the second arms are straight.

19. The delivery system of claim 15 wherein the first arms and the second arms are curved.

20. The delivery system of claim 15 wherein the connectors have fingers configured into a C-shape and the retainers are sleeves that fit over the C-shaped fingers in the locked position.

21. The delivery system of claim 15 wherein the connectors having a head and a neck, and the retainers are sleeves that fit over the heads in the locked position.

22. The delivery system of claim 15 wherein each first arm has an opening and the connectors are spring wires, and each spring wire has a base coupled to a corresponding first arm and a latch configured to be in the opening in the locked position.

23. The delivery system of claim 15 wherein each first arm is a tube and the connector is an opening at a distal portion of the tube, and each second arm is a rod within the tube and the retainer is a distal portion of the rod.

24. The delivery system of claim 15 wherein each connector comprises at least one flexible finger and a ball attached to the finger, and each second arm comprises a tube with the retainer comprising a distal portion of the tube.

25. The delivery catheter of claim 15 wherein the universal joint has a plurality of control wires, a spacer between the delivery catheter and the first and second arms, and flexible hinges coupling one side of the spacer to the delivery catheter and another side of the spacer to the first and second arms.

26. The delivery system of claim 25 wherein the flexible hinges include a first set of hinges coupling the one side of the spacer to the delivery catheter and a second set of hinges coupling the other side of the spacer to the first and second arms, and wherein the first set of hinges are circumferentially offset from the second set of hinges.

27. The delivery system of claim 15 wherein the universal joint has a ball coupled to the first and second arm and a socket in the delivery catheter configured to receive the ball.

28. The delivery system of claim 15 wherein the universal joint has (i) a flexible inner shaft coupled to the first and second arms and (ii) control wires.

29. A delivery system for implanting a medical device, comprising:
   a delivery catheter having a proximal portion and a distal portion;
   a connector mechanism having first arms and connectors, each first arm has an opening, a proximal portion coupled to the delivery catheter, and a distal portion, and each connector is at the distal portion of a corresponding first arm and configured to engage the medical device; and
   a locking mechanism having second arms and retainers, each second arm has a proximal portion coupled to the delivery catheter and a distal portion, and each retainer is at the distal portion of a corresponding second arm and configured to maintain engagement between the connector and the medical device in a locked position,
   wherein each first arm is associated with a corresponding second arm to define pairs of first and second arms in which the first arm and/or the second arm move relative to each other to a released position in which the retainer of the second arm is moved from the connector of the corresponding first arm to release the medical device, and
   wherein the connectors are spring wires, each spring wire has a base coupled to a corresponding first arm and a latch configured to be in the opening in the locked position.

30. A delivery system for implanting a medical device, comprising:
   a delivery catheter having a proximal portion and a distal portion;
   a connector mechanism having first arms and connectors, each first arm has a proximal portion coupled to the delivery catheter and a distal portion, and each connector is at the distal portion of a corresponding first arm and configured to engage the medical device; and
   a locking mechanism having second arms and retainers, each second arm has a proximal portion coupled to the delivery catheter and a distal portion, and each retainer is at the distal portion of a corresponding second arm and configured to maintain engagement between the connector and the medical device in a locked position,
   wherein each first arm is associated with a corresponding second arm to define pairs of first and second arms in which the first arm and/or the second arm move relative to each other to a released position in which the retainer of the second arm is moved from the connector of the corresponding first arm to release the medical device, and wherein each first arm is a tube and the connector is an opening at a distal portion of the tube, and each second arm is a rod within the tube and the retainer is a distal portion of the rod.

31. A delivery system for placing an implantable device, comprising:
a delivery catheter having a proximal portion and a distal portion; and
an attachment assembly having arm pairs in which individual arm pairs include a first arm with a connector and a second arm with a retainer, wherein (a) each first arm extends along a corresponding second arm, and (b) the first arm and/or the second arm moves relative to the other from a locked position in which the retainer interfaces with the connector to maintain engagement between the implantable device and the connector to a released position in which the retainer is positioned relative to the connector such that the implantable device can disengage the connector,
wherein each first arm has an opening and the connectors are spring wires, and each spring wire has a base coupled to a corresponding first arm and a latch configured to be in the opening in the locked position.

32. A delivery system for placing an implantable device, comprising:
a delivery catheter having a proximal portion and a distal portion; and
an attachment assembly having arm pairs in which individual arm pairs include a first arm with a connector and a second arm with a retainer, wherein (a) each first arm extends along a corresponding second arm, and (b) the first arm and/or the second arm moves relative to the other from a locked position in which the retainer interfaces with the connector to maintain engagement between the implantable device and the connector to a released position in which the retainer is positioned relative to the connector such that the implantable device can disengage the connector,
wherein each first arm is a tube and the connector is an opening at a distal portion of the tube, and each second arm is a rod within the tube and the retainer is a distal portion of the rod.

* * * * *